United States Patent
Yamane

(10) Patent No.: US 10,832,638 B2
(45) Date of Patent: *Nov. 10, 2020

(54) IMAGE DISPLAY DEVICE AND IMAGE DISPLAY SYSTEM

(71) Applicant: SONY CORPORATION, Tokyo (JP)

(72) Inventor: Kenji Yamane, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,357

(22) Filed: Jul. 31, 2019

(65) Prior Publication Data

US 2019/0355327 A1    Nov. 21, 2019

Related U.S. Application Data

(63) Continuation of application No. 15/967,783, filed on May 1, 2018, now Pat. No. 10,403,240, which is a continuation of application No. 14/665,703, filed on Mar. 23, 2015, now Pat. No. 9,966,045, which is a (Continued)

(30) Foreign Application Priority Data

Sep. 25, 2012   (JP) ................. 2012-210577

(51) Int. Cl.
| | |
|---|---|
| *G09G 5/377* | (2006.01) |
| *A61B 5/07* | (2006.01) |
| *G02B 21/36* | (2006.01) |
| *G06T 11/00* | (2006.01) |
| *A61B 5/00* | (2006.01) |
| *G09G 5/00* | (2006.01) |
| *G09B 11/00* | (2006.01) |
| *G01N 33/00* | (2006.01) |

(52) U.S. Cl.
CPC ............ *G09G 5/377* (2013.01); *A61B 5/742* (2013.01); *G02B 21/365* (2013.01); *G06T 11/00* (2013.01); *G01N 33/00* (2013.01); *G06T 2207/10056* (2013.01); *G06T 2207/20212* (2013.01); *G06T 2207/30004* (2013.01); *G09B 11/00* (2013.01); *G09G 5/00* (2013.01)

(58) Field of Classification Search
CPC ...... G09G 5/377; A61B 5/742; G02B 21/365; G06T 11/00
USPC ........................................................ 345/634
See application file for complete search history.

(56) References Cited

U.S. PATENT DOCUMENTS

| | | |
|---|---|---|
| 6,128,522 A | 10/2000 | Acker et al. |
| 2006/0008779 A1 | 1/2006 | Shand et al. |
| (Continued) | | |

FOREIGN PATENT DOCUMENTS

| | | | |
|---|---|---|---|
| JP | 2011-181015 | * | 9/2011 |
| JP | 2011-181015 A | | 9/2011 |

OTHER PUBLICATIONS

Non-Final Office Action for U.S. Appl. No. 13/973,339, dated Mar. 29, 2016, 23 pages.

(Continued)

*Primary Examiner* — Patricia I Young
(74) *Attorney, Agent, or Firm* — Chip Law Group

(57) ABSTRACT

There is provided an image display device including a display control unit having a display combining unit that displays one or a plurality of pathological index cursors based on information relating to a pathological slide image.

16 Claims, 11 Drawing Sheets

Related U.S. Application Data continuation of application No. 13/973,339, filed on Aug. 22, 2013, now Pat. No. 9,620,089.

(56) References Cited

U.S. PATENT DOCUMENTS

| | | | |
|---|---|---|---|
| 2008/0063136 A1* | 3/2008 | Ohyu | A61B 6/488 378/4 |
| 2009/0222746 A1 | 9/2009 | Chirica et al. | |
| 2012/0002033 A1 | 1/2012 | Yamane et al. | |

OTHER PUBLICATIONS

Final Office Action for U.S. Appl. No. 13/973,339, dated Jul. 15, 2016, 27 pages.
Advisory Action for U.S. Appl. No. 13/973,339, dated Sep. 22, 2016, 03 pages.
Notice of Allowance for U.S. Appl. No. 13/973,339, dated Dec. 6, 2016, 16 pages.
Non-Final Office Action for U.S. Appl. No. 14/665,703, dated May 24, 2017, 27 pages.
Final Office Action for U.S. Appl. No. 14/665,703, dated Oct. 12, 2017, 31 pages.
Notice of Allowance for U.S. Appl. No. 14/665,703, dated Jan. 12, 2018, 09 pages.
Non-Final Office Action for U.S. Appl. No. 15/967,783, dated Jun. 4, 2018, 17 pages.
Final Office Action for U.S. Appl. No. 15/967,783, dated Nov. 2, 2018, 18 pages.
Notice of Allowance for U.S. Appl. No. 15/967,783, dated May 1, 2019, 23 pages.

\* cited by examiner

1: DIGITAL MICROSCOPE
2: INFORMATION PROCESSING DEVICE
3: INFORMATION PROVISION DEVICE (SERVER)
4: IMAGE DISPLAY DEVICE
5: NETWORK

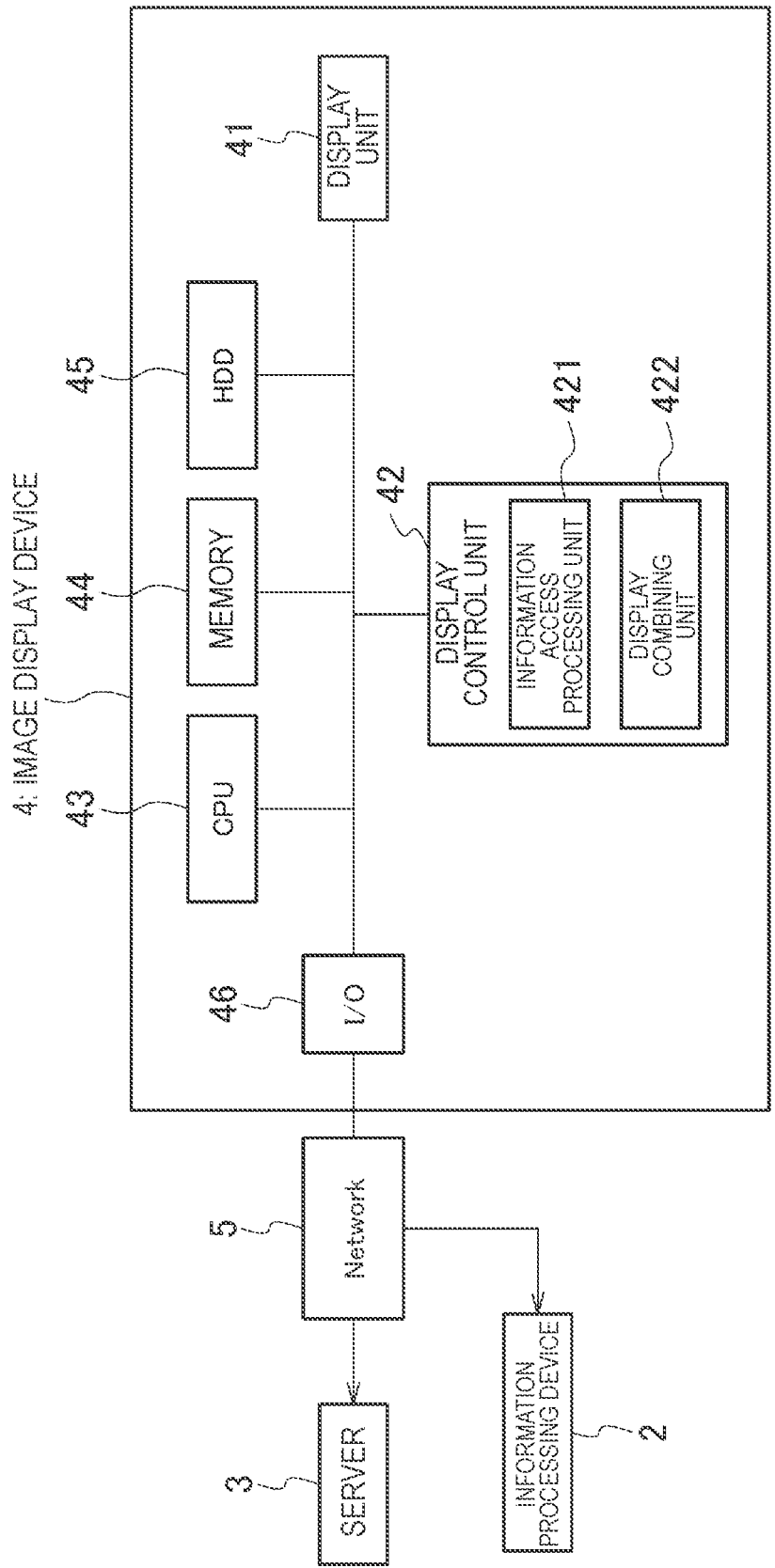

FIG. 6

```
START
   ↓
DATA RESPONSE UNIT INQUIRES OF SLIDE ID/CASE DATA
HOLDING UNIT BASED ON SLIDE ID AND SPECIFIES
CASE CORRESPONDING TO COMBINED IMAGE
   ↓
DATA RESPONSE UNIT ACQUIRES CANCER CASE LIST
CORRESPONDING TO CORRESPONDING SLIDE FROM
SLIDE ID/CASE DATA HOLDING UNIT
   ↓
DATA RESPONSE UNIT TRANSMITS
CANCER CASE LIST TO VIEWER
```

FIG. 7

| SLIDE ID | CASE |
|---|---|
| Slide01 | STOMACH CANCER |
| Slide02 | LUNG CANCER |
| Slide03 | COLON CANCER |

FIG. 8

| CASE | DISTANCE |
|---|---|
| STOMACH CANCER | 5mm, 10mm, 15mm |
| COLON CANCER | 10mm, 20mm, 30mm |
| LUNG CANCER | 15mm |

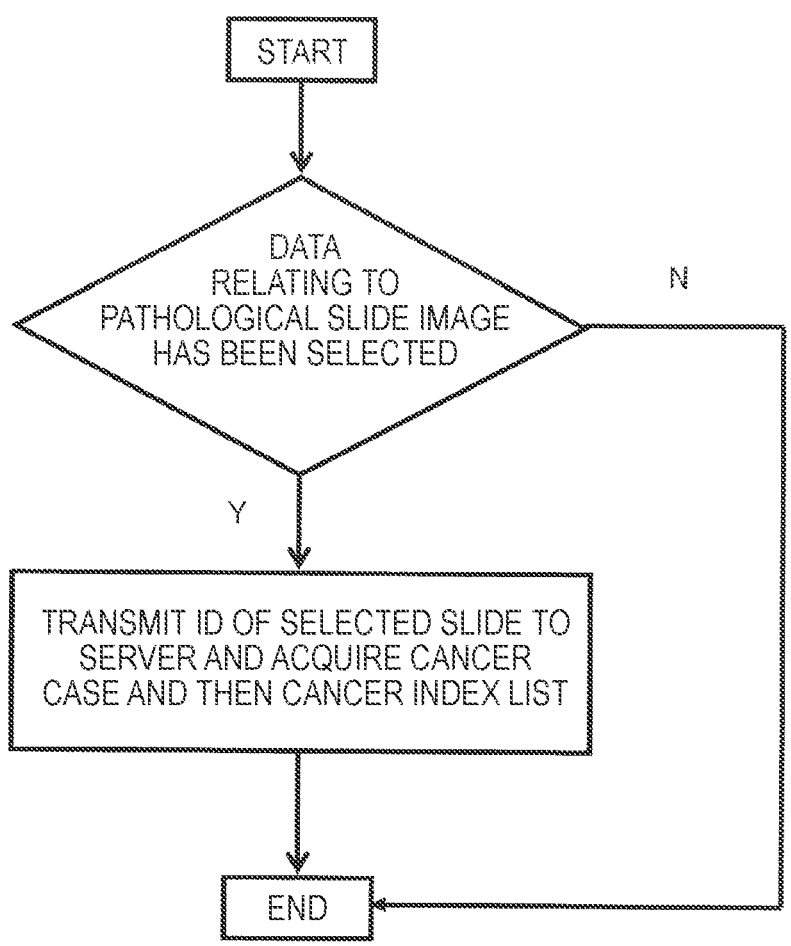

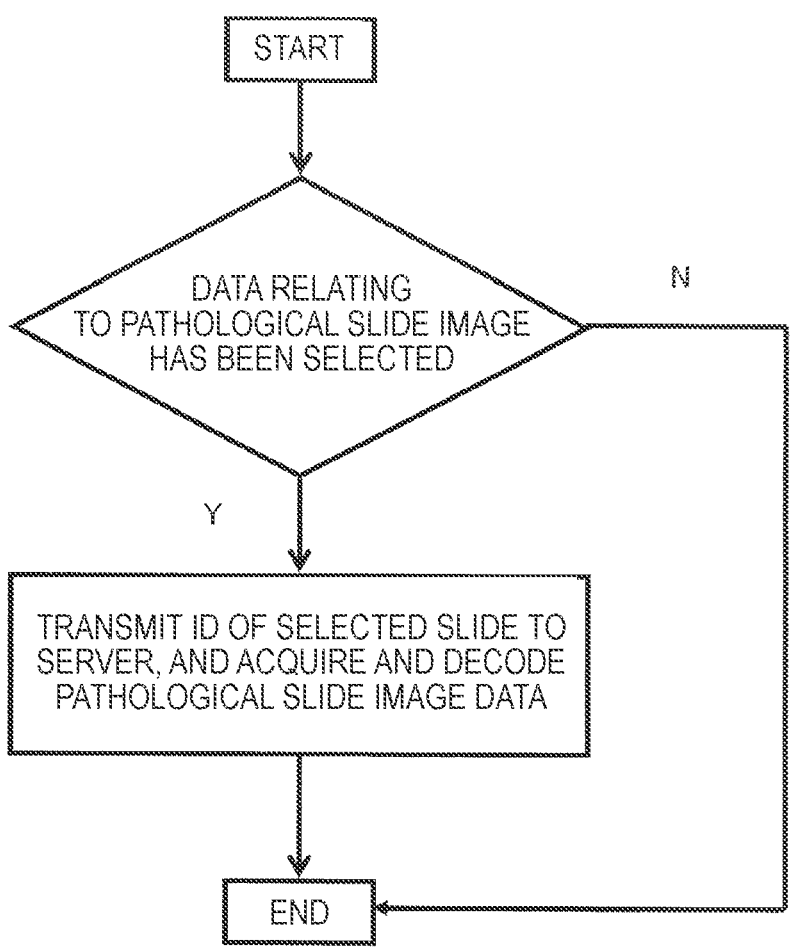

IMAGE DISPLAY DEVICE AND IMAGE DISPLAY SYSTEM

CROSS-REFERENCE TO RELATED APPLICATIONS

The present application is a continuation application of U.S. patent application Ser. No. 15/967,783, filed on May 1, 2018, which is a continuation application of U.S. patent application Ser. No. 14/665,703, filed on Mar. 23, 2015, now issued as U.S. Pat. No. 9,966,045, which is a continuation application of U.S. patent application Ser. No. 13/973,339, filed on Aug. 22, 2013, now issued as U.S. Pat. No. 9,620,089, which claims priority from prior Japanese Priority Patent Application JP 2012-210577 filed in the Japan Patent Office on Sep. 25, 2012, the entire content of which is hereby incorporated by reference.

BACKGROUND

The present disclosure relates to an image display device, an image display system, an image processing method, and a program that display an image captured by a microscope, and a microscope system capable of improving efficiency in case diagnosis. More particularly, the present disclosure relates to technology for improving efficiency in the diagnosis of a case employing a digital microscope.

In the fields of medicine, pathology, biology, materials, and the like, a technique of divisionally capturing an observation target area using a digital microscope and joining a plurality of obtained partial images together to obtain a wide view and high power microscopic observation image is in use. In a virtual microscope system using this technique, a user can cause an obtained microscopic observation image to be displayed at a random position and a random magnification, and can also cause the obtained microscopic observation image to be displayed at a remote place via a network. For such a reason, the technique is attracting attention particularly in the uses of biopsy and cell inspection in pathological diagnoses.

In the related art, a technique of displaying various kinds of information on a display unit together with a microscopic observation image (see Japanese Unexamined Patent Application Publication No. 2011-181015) has been proposed to improve convenience of a user, for example, in a medical institution.

In a pathological diagnosis system disclosed in Japanese Unexamined Patent Application Publication No. 2011-181015, a diagnosis-demanding area and the like is displayed in addition to a dyed sample image (microscopic observation image), and a user makes a pathological diagnosis while appropriately modifying the microscopic observation image and the image diagnosis-demanding area displayed on a display unit.

SUMMARY

However, in the existing virtual microscope system described above, a user himself or herself makes a final determination to appropriately modify an image diagnosis area displayed on a display unit, and makes a pathological diagnosis. In such a situation, there is insufficient information for the user to make most important case determinations, and a complicated separate manipulation on a screen is necessary to acquire or manipulate the information for making a case determination. In other words, it is difficult to say that efficiency in a diagnosis operation employing a digital microscope is improving.

It is desirable to provide an image display device, an image display system, a microscope system, an image processing method, and a program that is capable of improving a diagnosis operation employing a digital microscope and display an image captured by the microscope.

According to an embodiment of the present disclosure, there is provided an image display device including a display control unit having a display combining unit that displays one or a plurality of pathological index cursors based on information relating to a pathological slide image.

The display combining unit may change a size of a pathological index cursor according to a magnification of the pathological slide image.

The display combining unit may cause a pathological index cursor to blink and/or vary in color according to classification of cancer stages.

The display combining unit may display a rotatable and/or movable pathological index cursor.

The display combining unit may display a pathological slide image and a cancer index list for selecting the pathological index cursors.

The cancer index list may be one or two or more types of data selected from cancer invasion distance data, cancer invasion area data, cancer invasion depth data, cancer staining data, nucleo-cytoplasmic ratio data, etiological microbe number data, and cancer stage classification data.

The display control unit may further process data relating to a pathological slide image, cancer case data, and cancer index list data transmitted from an information provision device including a data response unit that acquires cancer index list data based on the information relating to the pathological slide image, and the image display device display the pathological slide image and the cancer index list.

The information provision device may further include an information holding unit that holds data relating to a pathological slide image, cancer case data, and cancer index list data corresponding to the pathological slide image data, and the data response unit may acquire the data relating to the pathological slide image, the cancer case data, and the cancer index list data corresponding to the pathological slide image from information holding unit based on the information relating to the pathological slide image, and transmit the acquired data to the display control unit.

According to an embodiment of the present disclosure, there is provided an image display system including an image display control unit having a display combining unit that displays one or a plurality of pathological index cursors based on information relating to a pathological slide image.

The image display system may further include an information provision device having a data response unit that acquires cancer case data and cancer index list data corresponding to the cancer case data based on the information relating to the pathological slide image.

According to an embodiment of the present disclosure, there is provided a microscope system including an image display system including an image display device having a display combining unit that displays one or a plurality of pathological index cursors based on information relating to a pathological slide image.

The image display system may further include an information provision device having a data response unit that acquires cancer case data and cancer index list data corresponding to the cancer case data based on the information relating to the pathological slide image, and transmits the acquired data to the image display device.

According to an embodiment of the present disclosure, there is provided an image processing method including displaying one or a plurality of pathological index cursors based on information relating to a pathological slide image.

The image processing method may further include acquiring cancer case data and cancer index list data corresponding to the cancer case data based on the information relating to the pathological slide image, and displaying the pathological slide image and a cancer index list for selecting the pathological index cursors based on the cancer case data and the cancer index list data corresponding to the cancer case data.

One or a plurality of pathological index cursors selected from the cancer index list may be displayed.

Cancer case data corresponding to the data relating to the pathological slide image and cancer index list data corresponding to the cancer case data may be acquired based on the information relating to the pathological slide image.

According to an embodiment of the present disclosure, there is provided a program causing an image display device to perform an information provision function of acquiring and transmitting cancer case data corresponding to information relating to a pathological slide image and cancer index list data corresponding to the cancer case data based on the information, and an image display function of displaying a cancer index list for selecting a pathological index cursor based on the cancer index list data.

According to an embodiment of the present disclosure, there is provided a program causing an image display device to perform an information provision function of holding data relating to a pathological slide image, cancer case data corresponding to the data relating to the pathological slide image and cancer index list data corresponding to the cancer case data, and acquiring and transmitting cancer case data corresponding to information relating to the pathological slide image and cancer index list data corresponding to the cancer case data based on the information, and an image display function of displaying a cancer index list for selecting a pathological index cursor based on the cancer index list data, and also displaying one or a plurality of pathological index cursors selected from the cancer index list.

According to the present disclosure described above, it is possible to improve efficiency in a diagnosis operation employing a digital microscope.

BRIEF DESCRIPTION OF THE DRAWINGS

FIG. 5 is a block diagram showing a configuration example of an image display device 4 shown in FIG. 1;

FIG. 6 is a flowchart illustrating transmission of various kinds of data of a cancer case list to the image display device 4 by a slide ID/case data holding unit 332;

FIG. 7 is a diagram showing a state in which an example of "slide ID—cancer case list" is shown on a display unit 41;

FIG. 8 is a diagram showing a state in which an example of "cancer case—cancer index list" is shown on the display unit 41;

FIG. 11 is a flowchart illustrating acquisition of various types of data relating to a pathological slide image (combined image) by a data selection/cancer index list data acquisition unit;

FIG. 12 is a flowchart illustrating acquisition and decoding of various types of data relating to a pathological slide image (combined image) by a data selection/cancer index list data acquisition unit;

DETAILED DESCRIPTION OF THE EMBODIMENT(S)

Figure 1:
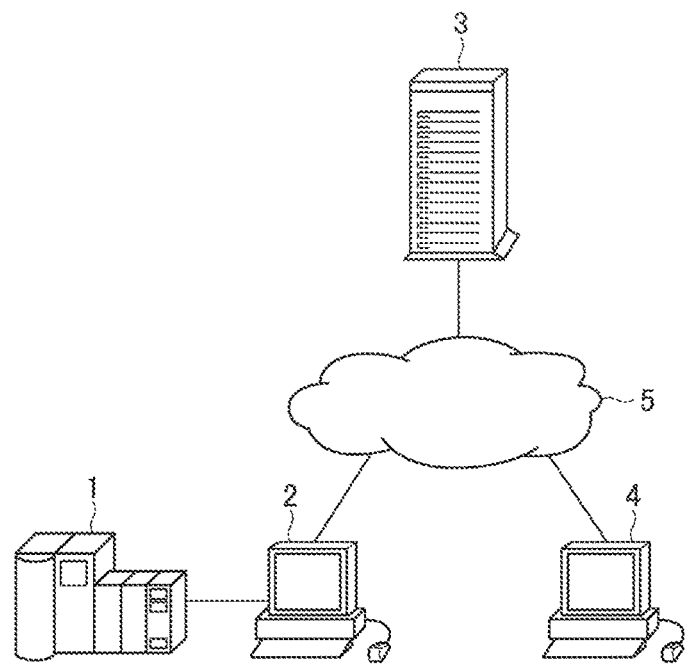
FIG. 1 is a diagram showing an outline of a microscope system according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. Description will be made in the following order.

1. First Embodiment of Present Disclosure

1. First Embodiment

[Configuration of Microscope System]

First, a virtual microscope system according to a first embodiment of the present disclosure will be described.

FIG. 1 is a diagram showing an outline of a microscope system of this embodiment. The microscope system of this embodiment is intended to capture and observe various prepared samples at a high magnification. The corresponding microscope system includes, for example, as shown in FIG. 1, a digital microscope 1, an information processing device 2, an information provision device (server) 3, an image display device 4, and the like.

In the microscope system of this embodiment, the information processing device 2 and the image display device 4 may be connected directly or via a network 5. Also, the information processing device 2 and the image display device 4 may be connected with the information provision device 3 via the network 5 to be able to communicate with the information provision device 3.

The information provision device 3 may double as the information processing device 2, or the information processing device 2 may double as the information provision device 3.

The image display device 4 may include the information processing device 2 and/or the information provision device 3. Since it is preferable to store various kinds of data in the information provision device 3, it is appropriate for the information display device 4 and the information provision device 3 to be separately configured in this embodiment.

Although only one of each device is shown in FIG. 1 for convenience to simplify the description, each device may be singular or plural in number, and the plurality of devices may be organically connected with each other. For example, when there are a plurality of image display devices, it is possible to share an image or information displayed on a screen among users in a medical institution or between a user and a patient.

The virtual microscope system of this embodiment can be applied in various fields such as medicine, pathology, biology, materials, and the like. For example, when the virtual microscope system of this embodiment is used for a pathological diagnosis, an observation object is an organ of a living body, tissue, cells, and the like, pieces of which are enclosed in prepared samples. For example, when the prepared sample is a pathological sample, a user of the image display device 4 (viewer of an image) is a doctor and the like, who makes a pathological diagnosis based on a displayed image.

Although, in the virtual microscope system of this embodiment, a user or the like makes a diagnosis of a case, status, and the like of cancer, it is important for this embodiment to have at least the image display device 4 according to an embodiment of the present disclosure, and further, it is appropriate to cooperate with the information provision device 3.

[Digital Microscope 1]

Figure 2:
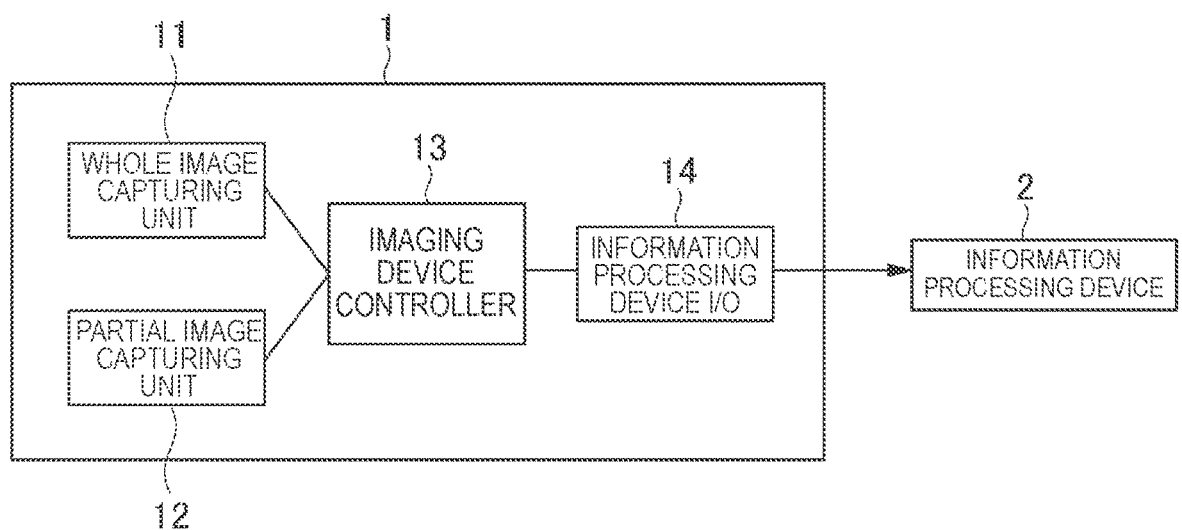
FIG. 2 is a block diagram showing a configuration example of a digital microscope 1 shown in FIG. 1.

A digital microscope 1 includes a light source, an objective lens, an image sensor, a stage, and the like, and radiates predetermined illumination light to a prepared sample placed on the stage to capture light transmitted through the observation object, light emitted from the observation object, or the like. FIG. 2 is a block diagram showing a configuration example of the digital microscope 1. As shown in FIG. 2, a whole image capturing unit 11 and a partial image capturing unit 12 are installed in the digital microscope 1 included in the microscope system of this embodiment.

The whole image capturing unit 11 includes a light source, a low power objective lens, a low resolution image sensor, and the like, and performs imaging of an entire observation target area of the prepared sample placed on the stage at a low magnification and a low resolution. On the other hand, the partial image capturing unit 12 includes a light source, a high power objective lens, a high resolution image sensor, and the like, and performs imaging of a part of the observation target area of the prepared sample placed on the stage at a high magnification and a high resolution. In other words, by the digital microscope 1, a low resolution whole image (thumbnail image) and a partial image (slide image) of a higher resolution than the whole image are captured.

In addition, an imaging device controller 13 that controls processing of imaging by the whole image capturing unit 11 and the partial image capturing unit 12, an input and output interface unit 14 for connecting to the information processing device 2, or the like may be installed in the digital microscope 1. By installing the input and output interface unit 14, it becomes possible to input a control command from the information processing device 2 or output respective pieces of data of images captured by the whole image capturing unit 11 and the partial image capturing unit 12 to the information processing device 2.

[Information Processing Device 2]

Figure 3:
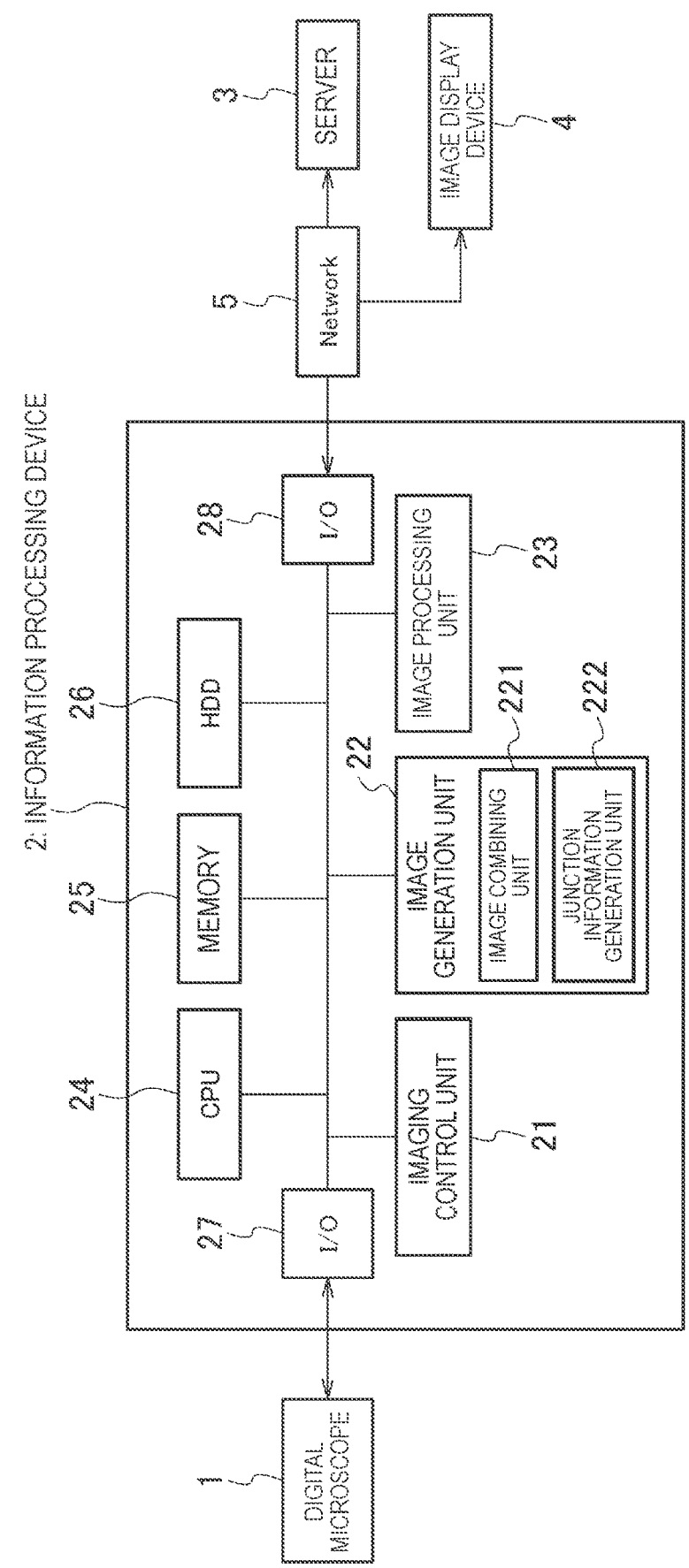
FIG. 3 is a block diagram showing a configuration example of an information processing device 2 shown in FIG. 1.

FIG. 3 is a block diagram showing a configuration of the information processing device 2. As shown in FIG. 3, an image generation unit 22 that joins partial images (slide images) captured by the digital microscope 1 together is installed in the information processing device 2. In addition, an imagingcontrol unit 21, an image processing unit 23, a central processing unit (CPU) 24, a memory 25, a hard disk 26, input and output interface units 27 and 28, and the like may be installed in the information processing device 2.

(Image Generation Unit 22)

Figure 4:
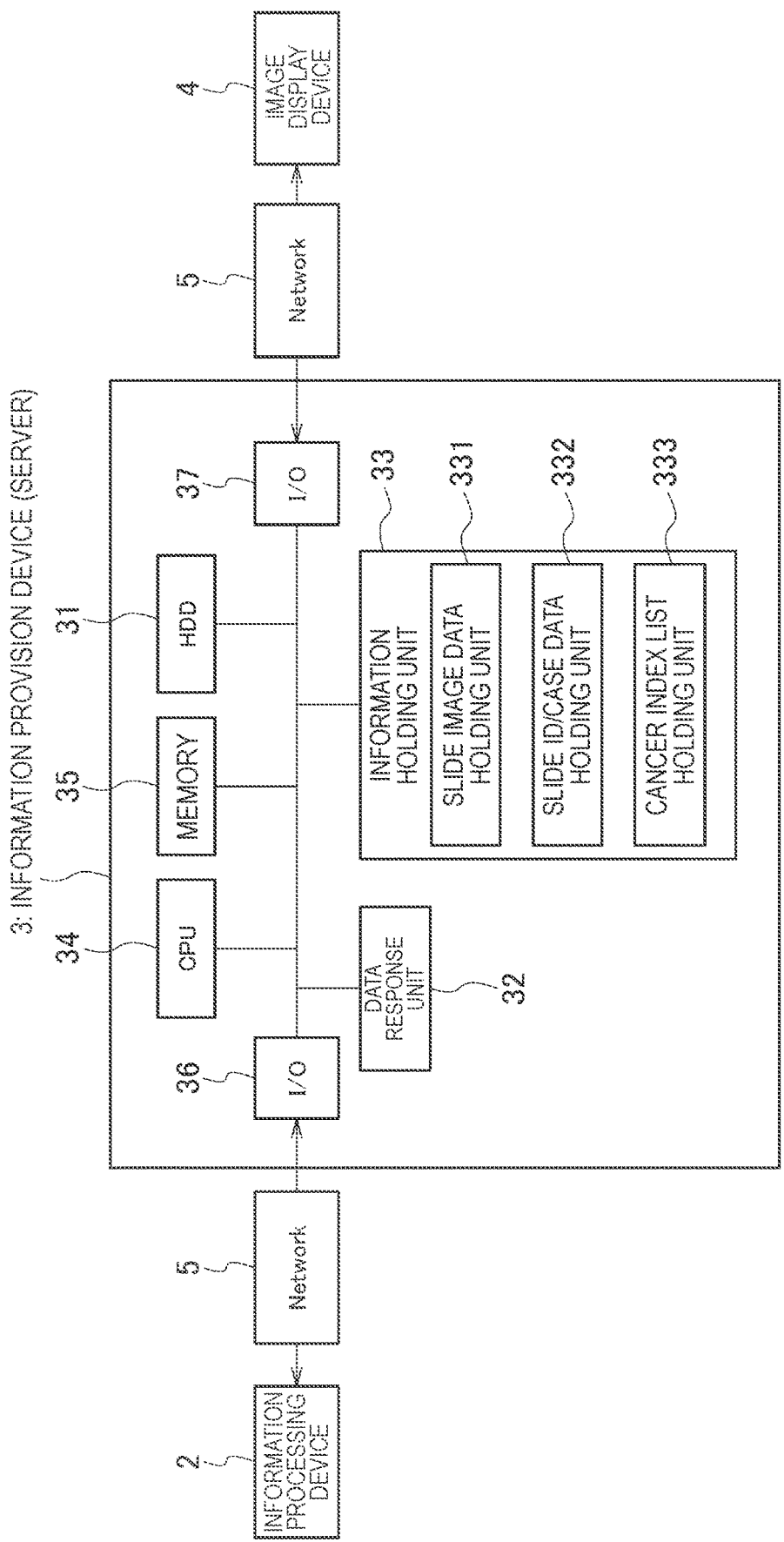
FIG. 4 is a block diagram showing a configuration example of an information provision device (server) 3 shown in FIG. 1.

FIG. 4 is a block diagram showing a configuration of the image generation unit 22. As shown in FIG. 4, the image generation unit 22 includes an image combining unit 221 that joins a plurality of partial images (slide images) in which parts of an observation target area are taken together, and a junction information generation unit 222 that generates junction information on a combined image combined by the image combining unit 221.

The image combining unit 221 joins the plurality of partial images (slide images) captured by the digital microscope 1 together to generate a high power, high resolution and wide view microscopic observation image (combined image). Specifically, a matching process is performed on the partial images to be joined (slide images), and the partial images (slide images) are joined together (stitched) based on a result of the matching process.

Also, the image combining unit 221 is capable of attaching identifiers to various kinds of slide image data such as a combined image (microscopic observation image) and the like to use the identifiers as information on pathological slide images.

Meanwhile, as the junction information on the combined image combined by the image combining unit 221, the junction information generation unit 222 generates, for example, information on junction positions of the respective partial images (slide images) and information on reliability of junction at the respective junction positions. In the junction information, information about presence or absence of a foreign substance or a position of a foreign substance may be included.

For example, as the junction reliability information, the relative amount of difference between adjacent partial images (slide images) caused by the stitching process may be acquired.

The combined image combined by the image combining unit 221 (wide view microscopic observation image) and the various kinds of junction information generated by the junction information generation unit 222 are output to the server 3 or the image display device 4 via the input and output interface unit 28 and the network 5.

(Imaging Control Unit 21)

The imaging control unit 21 can control driving of the digital microscope 1 upon capturing of a partial image (slide image), the whole image (thumbnail image), and the like, operation of the image generation unit 22 and the image processing unit 23, or the like.

(Image Processing Unit 23)

The image processing unit 23 performs an analysis of the whole image (thumbnail image) in which the entire observation target area is captured, construction of a sequence in which the digital microscope 1 captures partial images (imaging sequence), and the like. The imaging sequence constructed here is output to the imaging control unit 21.

(CPU 24)

The CPU 24 controls the respective units installed in the information processing device 2 overall, and executes a program that controls, for example, the image processing unit 23, the imaging control unit 21, and the like described above overall. Also, the CPU 24 can carry out calculation processes performed in the respective units of the information processing device 2, or carry out encoding of an image, a pattern matching process of partial images performed in the image combining unit 221, and the like.

(Memory 25)

The memory 25 is used as a work area of the CPU 24, and temporarily stores the partial images (slide images), the whole image (thumbnail image), and the like that are captured by the digital microscope 1 and input from the input and output interface unit 27.

(Hard Disk 26)

In the hard disk 26, for example, processing results (imaging sequence and the like) of the image processing unit 23 and the like, the combined image combined by the image combining unit 221 (wide view microscopic observation image), the junction information generated by the junction information generation unit 222, and the like are stored.

In addition, a computer program for implementing the respective functions of the information processing device 2 described above can be created and installed in a personal computer and the like. Such a computer program may be stored in storage media, for example, a magnetic disk, an optical disc, a magneto-optical disc, a flash memory, and the like, and can also be delivered via a network.

[Information Provision Device (Server) 3]

The information provision device 3 manages various kinds of data uploaded from the information processing device 2, and outputs the various kinds of data to the image display device 4 or the information processing device 2 in response to a request.

FIG. 4 is a block diagram showing a configuration example of the information provision device 3. As shown in FIG. 4, the information provision device (server) 3 is connected with the information processing device 2 and the image display device 4 via the network 5. The information provision device (server) 3 includes a hard disk 31, a data response unit 32, an information holding unit 33, a CPU 34, a memory 35, input and output interface units 36 and 37, and the like.

(Data Response Unit 32)

The data response unit 32 can request the information processing device 2 to transmit various kinds of data, such as data relating to the combined image and the like, and causes the information holding unit 33 to store the various kinds of data received from the information processing device 2.

As the data relating to the combined image, there are various kinds of data, for example, combined image (wide view microscopic observation image) and junction information, a low resolution whole image (thumbnail image), partial images to be joined (slide images), imaging sequence information, and the like.

Hereinafter, "combined image (wide view microscopic observation image)" is also referred to as "pathological slide image," "combined image," or "combined image (observation image)."

In addition, "low resolution whole image (thumbnail image)" is also referred to as "whole image (thumbnail image)."

Furthermore, "partial images to be joined (slide images)" are also referred to as "partial images" or "partial images (slide images)."

For example, the data response unit 32 may cause the information processing device 2 to transmit a pathological slide image through data segmentation such as packet transmission or the like, receive the data, and then recover the pathological slide image from the data. Also, the data response unit 32 may cause the information processing device 2 to transmit partial images and imaging sequence information, receive the partial images and the imaging sequence information, and then recover a pathological slide image from the partial images based on an imaging sequence of the imaging sequence information.

In addition, a user or the like selects a slide ID, such that the data response unit 32 can request the information holding unit 33 storing various kinds of data to transmit various kinds of data corresponding to the slide ID to the information processing device 2, the image display device 4, and the like.

For example, as shown in FIG. 6, a user or the like selects a slide ID when making a diagnosis, such that the data response unit 32 requests "a cancer case" corresponding to the slide ID from the information holding unit 33 and specifies "a cancer case." Also, the data response unit 32 transmits data of "the slide ID and the cancer case" to the image display device 4. Since the corresponding various kinds of data are displayed as a combined image (for example, see FIG. 7), it becomes easy for the user to check the slide ID and the medical case, and mistakes such as misunderstanding of a sample in use and the like can be reduced.

Furthermore, by deciding "a cancer case," the data response unit 32 searches for and specifies one or a plurality of "cancer index lists" that have been stored in the information holding unit 33 in advance and correspond to the cancer case. Also, the data response unit 32 transmits data of the one or plurality of "cancer index lists" to the image display device 4. The "cancer index lists" are displayed (for example, see FIG. 8), and thus it is possible to display an index used in one or a plurality of diagnoses of cancer, such that efficiency in a cancer diagnosis operation of the user is improved.

(Information Holding Unit 33)

The information holding unit 33 can store various kinds of data such as data relating to the above-described combined image transmitted from the information processing device 2, data processed by the image display device 4, and the like.

The information holding unit 33 includes a slide image data holding unit 331, a slide ID/case data holding unit 332, and a cancer index list holding unit 333, and stores and holds various kinds of data in the respective units. Also, the information holding unit 33 is controlled by the data response unit 32, such that the corresponding data response unit 32 can have control over a process of reading and writing various kinds of data held in the information holding unit 33, an image combining process, and the like.

(Slide Image Data Holding Unit 331)

In the slide image data holding unit 331, the above-described data relating to the pathological slide image and an identifier attached to the data are stored. Also, the slide image data holding unit 331 can link an identifier to data relating to a stored pathological slide image. The linking makes it possible to obtain information relating to the pathological slide image.

(Slide ID/Case Data Holding Unit 332)

In the slide ID/case data holding unit 332, a slide ID of data relating to one pathological slide image and data of one cancer case corresponding to the data relating to the pathological slide image are stored in connection with each other (for example, see FIG. 6). By selection of a user or the like, data of a plurality of cancer cases corresponding to data relating to one pathological slide image may be stored in connection with the data relating to the pathological slide image.

A "slide ID" may be a random number input by a user or the like, or the slide ID/case data holding unit 322 or the data response unit 32 may select and combine the "slide ID" from among a patient number, a check-up date, a check-up number, a check-up item, a sample number, a branch number of the sample number, a random number of the user, and the like. Preferably, the patient number and the like are stored in the information provision device 3.

Although this will be described later, a "cancer case" refers to a case of cancer such as stomach cancer, lung cancer, colon cancer, and the like.

Data of a "slide ID" and/or "cancer case" can be linked to combined image data as an "identifier" by the slide ID/case data holding unit 322 or the data response unit 32. In this linked state, the data of a "slide ID" and/or "cancer case" and the combined image data may be stored in the slide ID/case data holding unit 332.

"Linking" of an identifier of a slide ID or the like may be performed by an input of a user or the like when a clinical material is observed through a microscope, when combined image data is processed, etc. Also, linking of an "identifier" to a check-up item, a patient number, a check-up date, and one or two or more selected from among a check-up number, a sample number, and a branch number of the sample number may be performed by the data response unit 32. The linking makes it possible to obtain information relating to the pathological slide image.

As an example, the data response unit 32 requests the data relating to the combined image and the like from the information processing device 2 that stores the data of the combined image and the like, and requests a check-up item, a check-up number, and the like corresponding to the requested data from the information holding unit 33. Also, the data response unit 32 combines an identifier with pathological slide image data—"slide 01—stomach cancer" and the like such that the identifier is attached to the pathological slide image data. For this reason, it is possible to obtain information relating to the pathological slide image. The data (information) is held in the information holding unit 33.

When pathological slide image data is not held in the information provision device 3, the data response unit 32 can request pathological slide image data from one device (for example, the information processing device 2) by selecting an identifier such as "slide 01—stomach cancer" or the like. Also, the data response unit 32 can transmit the pathological slide image data to the image display device 4 and display the pathological slide image data on a display unit 41.

(Cancer Index List Holding Unit 333)

In the cancer index list holding unit 333, cancer index lists that are various lists used as indices to diagnose cancer are stored.

Cancers diagnosed by the present disclosure are not particularly limited. For example, the cancers diagnosed by the present disclosure include brain tumors, breast cancer, cervical cancer, ovarian cancer, esophageal cancer, stomach cancer, colon cancer, anal cancer, liver cancer, pancreatic cancer, laryngeal cancer, oral cancer, tongue cancer, thyroid cancer, kidney cancer, lung cancer, osteosarcomas, prostate cancer, testicular tumors, renal cell carcinomas, bladder cancer, rhabdomyosarcomas, skin cancer, leukemia, and the like.

Since it is known that viral or bacterial infections are involved in these cancers, examination of etiological microbes is also important in diagnosis (examination) of cancer. For example, human papilloma viruses type 16 and type 18 are implicated in cervical squamous cell cancer; human T-cell lymphotropic virus is implicated in adult T-cell leukemia; hepatitis B virus (HBV) is implicated in hepatocellular carcinomas; hepatitis C virus (HCV); *Helicobacter pylori* is implicated in stomach cancer; and the like.

As an index generally used in diagnosis of cancer, TNM classification of the Union for International Cancer Control (UICC) is internationally used. In Japan, classification of disease stages based on "Classification of disease stages according to stomach cancer handling agreement," "Colon cancer handling agreement," and the like arranged by academic associations, the Ministry of Health, Labour and Welfare, and the like is widely used.

When a cancer diagnosis is made, a region, a size of a clinical material, naked eye classification, a size of a lesion, a histological type, an invasion depth, lymphatic vessel invasion, vein invasion, a horizontal margin (distance), a vertical margin (distance), and the like are checked.

A "cancer index list" according to an embodiment of the present disclosure is obtained by listing classified disease stages generally used in diagnosis of cancer as described above according to each cancer case.

In a cancer index list according to an embodiment of the present disclosure, invasion distance of cancer, invasion depth of cancer, cancer staining, a nucleo-cytoplasmic ratio, etiological microbes, classification of cancer stages, and the like are written regarding each cancer case. Using the cancer index list according to an embodiment of the present disclosure as a reference, a user (doctor or the like) or the like can diagnose the status of cancer.

"Cancer staining" indicates staining of cancer tissue, and includes immunohistochemical staining, staining with a dye such as Lugol dye, and the like.

Data of one or a plurality of classified disease stages of each cancer case is stored and held in the cancer index list holding unit 333 as the "cancer index list" according to an embodiment of the present disclosure. The "cancer index list" can be input in advance and held. When the "cancer index list" is selected, data relating to the "cancer index list" can be acquired based on a "case of cancer" and the "cancer index list" from a homepage of an academic association and the like via a network.

A detailed "cancer index list" includes, for example, data of cancer invasion distance, data of cancer invasion area, data of cancer invasion depth, cancer staining data, nucleo-cytoplasmic ratio data, cancer-causing microbe number data, cancer stage classification data, and the like. One or two or more selected from among these pieces of data may be used. These are mainly used to diagnose cancer based on length and/or color.

One or a plurality of "cancer index lists" are attached to each case of cancer. For example, referring to FIG. 8, a cancer invasion distance list of "5 mm, 10 mm, and 15 mm" that is one cancer index list is displayed in "stomach cancer" that is one case of cancer.

For this reason, by selecting a "slide ID" or a "case of cancer" attached to combined image data as an identifier, one or a plurality of cancer index lists corresponding to the case of cancer are displayed on the display unit 41.

When two or more index lists correspond to one case of cancer, a sequence of displayed index lists can be set in advance by a user or the like. Also, the sequence of displayed index lists may be set such that cancer index lists corresponding to a check-up item are displayed by priority.

For example, when cancer cell staining is a check-up item, cancer staining data is automatically moved upward in a cancer index list. Also, when a check-up item is for seeing cancer invasion, data of cancer invasion distance, data of cancer invasion area, and data of cancer invasion depth are automatically moved upward.

When a check-up item is for observing etiological microbes, cancer-causing microbe number data is moved upward. Also, when a check-up item is for observing cancer cells with a microscope, nucleo-cytoplasmic ratio data obtained by dividing the volume of the nucleus of a cell by the volume of the cytoplasm is automatically moved upward.

In addition, since cancer stages are generally classified as diagnosis results, cancer stage classification data may be shown upward, or prepared as a symbol that can be easily selected by a user.

(CPU 34)

The CPU 34 controls the respective units installed in the information provision device 3 overall, and thus executes a program that controls the data response unit 32, the information holding unit 33, and the like described above overall. Also, the CPU 34 can carry out calculation processes performed in the respective units of the information provision device 3, or carry out encoding of an image, a pattern matching process of partial images performed in an image combining unit, and the like.

(Memory 35)

The memory 35 is used as a work area of the CPU 34, and temporarily stores the partial images (slide images), the whole image (thumbnail image), a slide ID, a case of cancer, a cancer index list, and the like that are transmitted from the outside and input through the input and output interface units 36 and 37.

(Hard Disk 31)

In the hard disk 31, for example, processing results of the data response unit 32 and the like are stored.

In addition, a computer program for implementing the respective functions of the information provision device 3 described above can be created and executed in a personal computer and the like. Such a computer program may be stored in storage media, for example, a magnetic disk, an optical disc, a magneto-optical disc, a flash memory, and the like, and can also be delivered via a network.

Here, the information provision device 3 described above can be included in the image display device 4 as an information provision unit.

[Image Display Device 4]

FIG. 5 is a block diagram showing a configuration example of the image display device 4. As shown in FIG. 5, the image display device 4 is connected with the information processing device 2 and/or the information provision device (server) 3 via a network. The image display device 4 includes the display unit 41, a display control unit 42, a CPU 43, a memory 44, a hard disk 45, an input and output interface unit 46, and the like.

Using an input device (not shown) such as a keyboard, a pointing device (mouse, trackball, touchpad, and the like), and the like, it is possible to input information (text and the like) to the image display device 4 or perform point and click. When the display unit 41 is in the form of a touch panel, it is possible to make an input or perform point and click on a screen.

(Display Unit 41)

The display unit 41 displays information for performing a diagnosis operation employing a digital microscope, and enables the corresponding information to be read. Displayed information includes, for example, a clinical material image such as a combined image, a slide ID, a cancer index list, a pathological index cursor, and the like. As display information, a pathological slide image (clinical material image), a slide ID, and a cancer index list may be appropriately displayed in combination, and the display information may be, for example, a list of "slide ID—cancer cases," a list of "cancer case—cancer index lists," and the like.

For example, when a cancer diagnosis operation is performed, a pathological slide image, cancer index lists for selecting the aforementioned cursor, and the like are displayed in the display unit 41 as shown in FIGS. 9A, 9B, 10A, 10B and 10C. By selecting one cancer index list for selecting the aforementioned cursor, a mouse pointer is turned into a pathological index cursor (for example, in the form of a ruler, a seal, or the like) and displayed. In the case of a ruler form, the length, size, direction and the like of the ruler may be changed according to the selected cancer index list. Also, in the case of a seal form, a seal can blink, vary in color, and function as a description frame according to the selected cancer index list.

Also, by selecting one of the cancer index lists for selecting the aforementioned cursor, a new pathological index cursor may be displayed with no change in the mouse pointer, and in this case, it is possible to handle the cursor using a plurality of pointing devices or by touch manipulation.

(Display Control Unit 42)

The display control unit 42 includes an information access processing unit 421 and a display combining unit 422, and controls these overall.

The information access processing unit 421 requests and acquires various kinds of necessary data from the information provision device (server) 3 having the data response unit 32 and the information holding unit 33 based on information relating to pathological slide image data (an identifier attached to the data relating to a pathological slide image). At this time, cancer case data, the cancer index list data, and the data relating to a pathological slide image (combined image) requested by the information access processing unit 421 is transmitted from the information provision device 3.

The display combining unit 422 of the display control unit 42 processes various kinds of data such as the transmitted cancer case data, cancer index list data, and the like, and displays a processed image (pathological slide image, cancer index list, pathological index cursor, and the like), text information, or the like in the display unit 41.

(Information Access Processing Unit 421)

The information access processing unit 421 requests the information provision device 3 to transmit various kinds of data such as the data relating to the combined image, the cancer index list data, the slide ID data, and the like to the image display device 4. The information access processing unit 421 may hold the various kinds of acquired data in the HDD 45, the memory 44, or the like of the image display device 4 as necessary. Also, the information access processing unit 421 may perform processing such as decoding (recovery) of the various kinds of acquired data.

In addition, the information access processing unit 421 may include a combined image-related data selection/cancer index list data acquisition unit and a combined image-related data request/decoding unit (not shown). Preparation of these improves operational efficiency.

Hereinafter, the combined image-related data selection/cancer index list data acquisition unit will be referred to as a "data selection/acquisition unit," and the combined image-related data request/decoding unit will be referred to as a "request/decoding unit."

[Combined Image-Related Data Selection/Cancer Index List Data Acquisition Unit]

Figure 13:
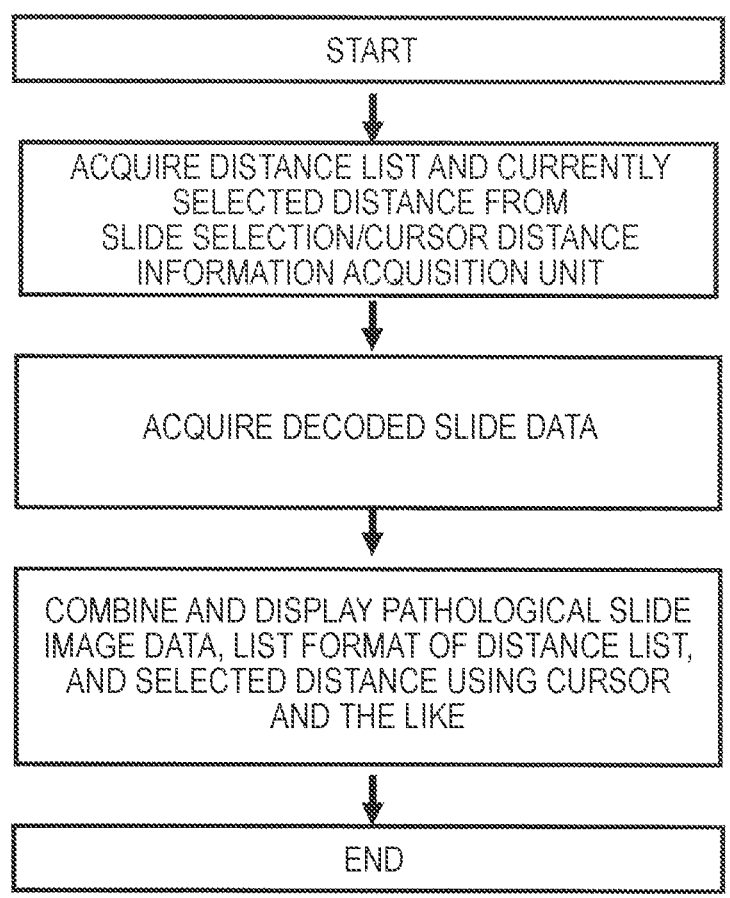
FIG. 13 is a flowchart illustrating acquisition of data relating to a combined image and decoding of the combined image by a slide image data selection/decoding unit.
Figure 14:
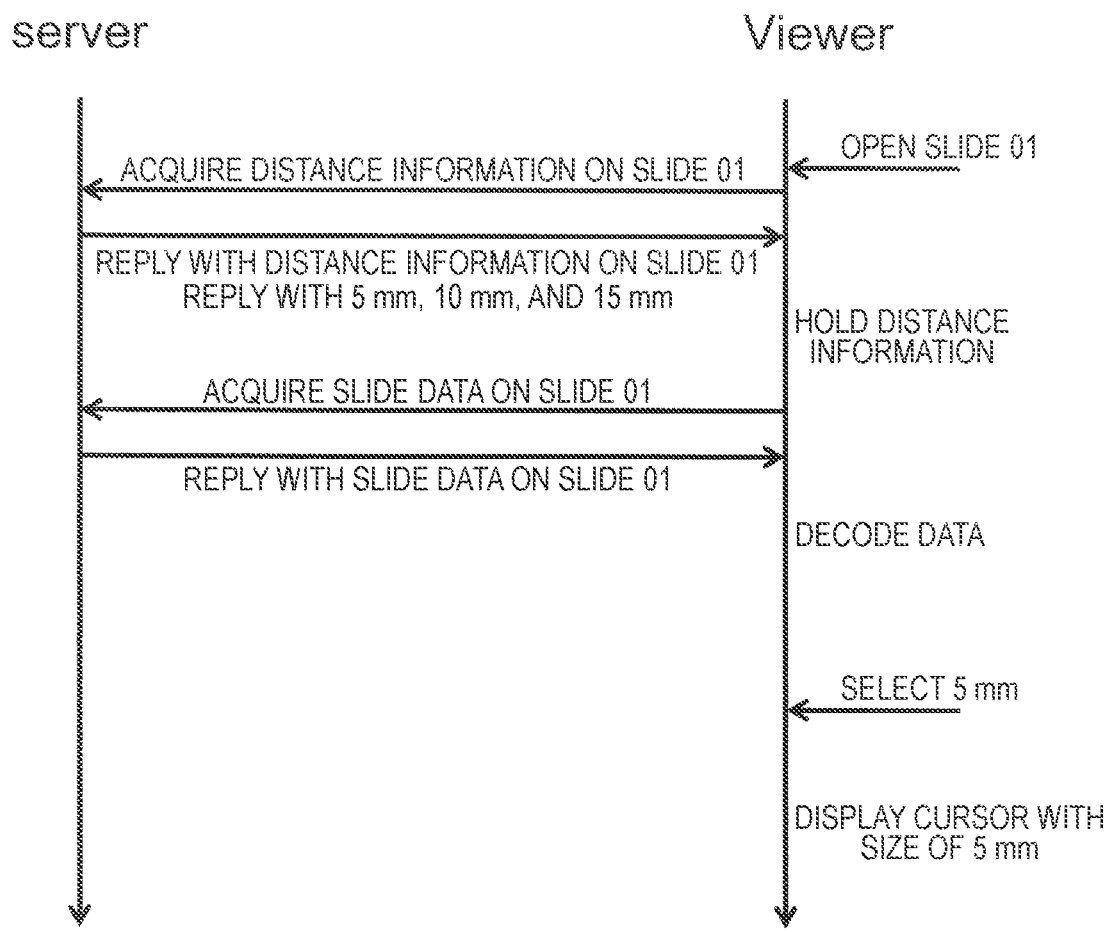
FIG. 14 is a flowchart for displaying a pathological index cursor.

When a user or the like selects the data relating to the combined image displayed in the display unit 41, the corresponding slide ID is decided by the data selection/acquisition unit as shown in FIGS. 11 to 13. This decision causes the information provision device 3 to search for a cancer case based on information relating to a pathological slide image (an identifier such as a slide ID or the like). In addition, the data selection/acquisition unit requests the information provision device 3 to transmit a result of searching for one or plurality of cancer case lists corresponding to the information relating to the pathological slide image (an identifier of a cancer case or the like) based on the information. By the request of the data selection/acquisition unit, the image display device 4 acquires slide ID data, cancer case data, and data of the one or plurality of cancer case lists corresponding to the cancer case based on the information relating to the pathological slide image (the identifier). Furthermore, the data selection/acquisition unit can hold these acquired pieces of data in the HDD 45 or the like.

These acquired pieces of data are combined with necessary information such as a list of "slide ID—cancer cases," a list of "cancer case—cancer index lists," a "cancer index list," and the like by the display control unit 42. In this way, a combined image, text information or the like of a "slide ID—cancer case list," a "cancer case—cancer index list," a "cancer index list," and the like is displayed in the display unit 41.

When a user or the like does not select data relating to the combined image but selects an identifier (for example, a slide ID, a cancer case, or the like), the data selection/acquisition unit can request and acquire various kinds of data from the information provision device 3 based on the identifier. These acquired pieces of data are combined with necessary information such as the list of "slide ID—cancer cases," the list of "cancer case—cancer index lists," the "cancer index list," and the like by the display control unit 42.

[Slide Image Data Request/Decoding Unit]

As shown in FIG. 12, a user or the like selects a whole image (thumbnail image) displayed in the display unit 41. When the whole image (thumbnail image) is selected, the corresponding slide ID is decided, and the request/decoding unit transmits the slide ID to the information provision device 3, acquires various kinds of data such as data relating to a necessary combined image and the like, and decodes (recovers) the acquired data as necessary. The request/decoding unit can acquire pathological slide image data from the information provision device 3, recover the pathological slide image data, and transmit the recovered image to the display combining unit 422 that will be described below. These pieces of data are combined with a pathological slide image (combined image) by the display combining unit 422.

In addition, the user or the like selects a slide ID from a list of "whole image (thumbnail image)—slide IDs" or a list of slide IDs. In this way, the request/decoding unit can acquire various kinds of data relating to an image from the information provision device 3 and decode the acquired data.

(Display Combining Unit 422)

Based on information relating to the pathological slide image such as the slide ID selected by the user or the like, combined image data, or the like, the display combining unit 422 requests and acquires various kinds of necessary data from the information provision device 3. At this time, various kinds of data in the information relating to the pathological slide image are combined with a cancer case list, the combined image, a cancer index list, and the like by the information access processing unit 421 and transmitted to the display combining unit 422. Here, the slide ID, a cancer case, and the like may function as an identifier attached to the pathological slide image data.

The display combining unit 422 displays a cancer index list for selecting a pathological slide image (combined image) and a pathological index cursor in the display unit 41.

When one cancer index is selected from a cancer index list, the display combining unit 422 combines a pathological index cursor corresponding to the cancer index list.

The display combining unit 422 can decide a size of a pathological index cursor based on a size of the slide combined image or the whole image acquired from the information provision device 3 or the like. Expansion and contraction of a pathological index cursor corresponding to the image may be held in advance in a memory, a storage unit, or the like.

Specifically, when the user selects determination based on distance, area, and the like such as cancer invasion distance data, cancer invasion area data, cancer invasion depth data and the like, a pathological index cursor that is in the form of a ruler whereby a distance or an area can be calculated and corresponds to a size of the combined image or the like is decided. The pathological index cursor in the form of a ruler is combined in the display combining unit 422 and displayed in the display unit 41. Shapes of the pathological index cursor in the form of a ruler are not particularly limited, and include, for example, a triangular shape, a quadrangular shape, a square shape, an oval shape, a circular shape, and the like. The pathological index cursor in the form of a ruler with gradations is appropriate for improving efficiency in a diagnosis operation.

When the user selects determination based on a value such as a number, a ratio, and the like including cancer staining data, nucleo-cytoplasmic ratio data, cancer-causing microbe number data, and the like, a pathological index cursor in the form of a seal whose value can be determined and that corresponds to a size of the combined image or the like is decided. The pathological index cursor in the form of a seal is combined in the display combining unit 422 and displayed in the display unit 41. Forms of the seal are not particularly limited. For example, the seal may blink and/or vary in color to facilitate determination of the value, or a total of numbers or the degree of a ratio may be attached around the seal. Also, the seal may be displayed as an arrow and/or a frame for displaying text information.

When a determination is made based on cancer stage classification data, a picture or a value for determining a stage may be displayed, or the determination can be derived from the aforementioned cancer invasion distance data, cancer invasion area data, cancer invasion depth data, cancer staining data, nucleo-cytoplasmic ratio data, cancer-causing microbe number data, and the like.

In addition, when a cancer index serving as a pathological index cursor in the form of a ruler is selected from a cancer index list, and further, a disease stage is selected, the display combining unit 422 decides a size of the pathological index cursor to correspond to the size and combines the pathological index cursor with the combined image.

When a cancer index serving as a pathological index cursor in the form of a seal is selected from a cancer index list, the display combining unit 422 decides a size of the pathological index cursor to correspond to a size of the combined image and combines the pathological index cursor with the combined image.

When the user or the like changes a display magnification of the displayed combined image, the display combining unit 422 can change a size of a pathological index cursor according to the display magnification of the pathological slide image. In this way, it is possible to improve a cancer diagnosis operation and also reduce misdiagnoses.

Also, the display combining unit 422 may set a pathological index cursor to be rotatable and/or movable and display the pathological index cursor in the display unit 41. In this way, it becomes possible to appropriately select a direction of an arrow according to a shape of a cancer region to be examined, and efficiency in a diagnosis operation improves.

Further, the display combining unit 422 can set a displayed pathological index cursor to blink and/or vary in color according to a classified stage of cancer. In this way, for example, when a number or size becomes a predetermined value (threshold) or more, a pathological index cursor blinks or varies in color, such that it becomes easy to understand a classified disease stage, and efficiency in a diagnosis operation improves.

Next, an image processing method of performing a display using the microscope system of this embodiment such that a cancer diagnosis operation can be performed will be described. In particular, a basic operation in an image display process by the image display device 4 will be described.

[Operation 1]

When a user selects a slide ID of data relating to a combined image in the image display device 4, the display control unit 42 acquires one or a plurality of cancer case lists based on information relating to a pathological slide image (for example, a linked slide ID or the like).

When a user selects information relating to a pathological slide image (for example, a slide ID or the like) in the image display device 4, the display control unit 42 acquires data relating to the pathological slide image (combined image) based on information relating to the corresponding pathological image (for example, the slide ID or the like). At this time, data such as a size of a sample, a size of the combined image, and the like is included.

The display control unit 42 controls the acquired and combined pathological slide image (combined image) and one or a plurality of case lists to be displayed. When the user selects any one of classified disease stages of a case list, a pathological index cursor is combined with the combined image and displayed. At this time, a size of the pathological index cursor is decided in consideration of a size of a sample and a size of the pathological slide image (combined image). For example, in the case of a pathological index cursor in the form of a ruler, a length such as a currently selected cancer invasion distance and the like is calculated in consideration of the size of the sample and the size of the combined image, and the pathological index cursor with the size of the cursor is combined with the combined image and displayed.

The display control unit 42 may automatically select any of classified disease stages of a case list or the lowest of the disease stages, and a pathological index cursor corresponding to the selected disease stage may be combined with the combined image and displayed.

Figure 9A:
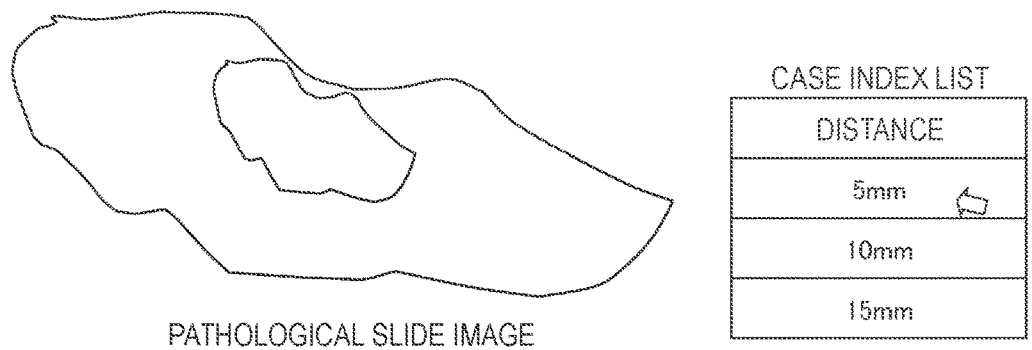
FIGS. 9A and 9B are diagrams showing a state in which "pathological slide image a," "cancer index list b," and "pathological index cursor c" are displayed on the display unit 41 in the form of a cursor.
Figure 9B:
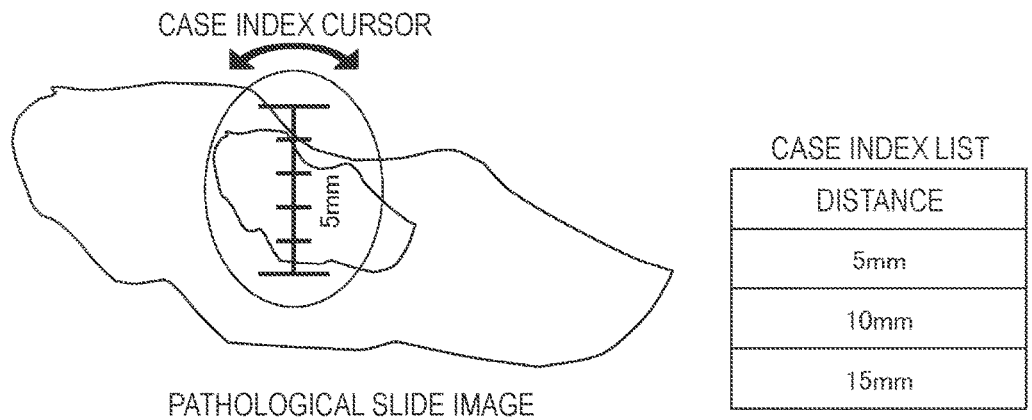
Figure 10A:
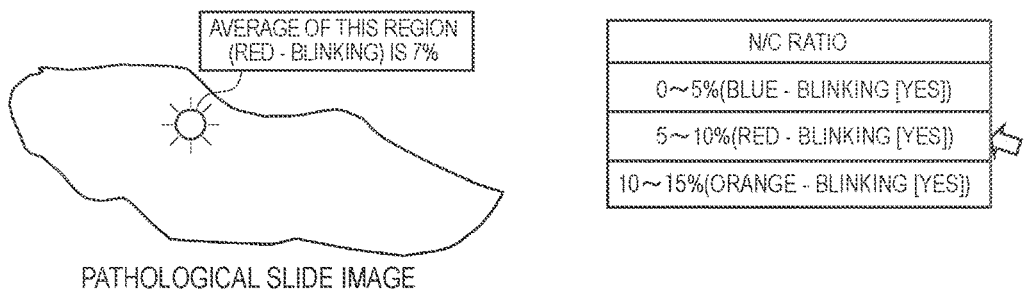
FIGS. 10A, 10B, and 10C are diagrams showing a state in which "pathological slide image a," "cancer index list b," and "pathological index cursor c" are displayed on the display unit 41 in the form of an arrow.
Figure 10B:
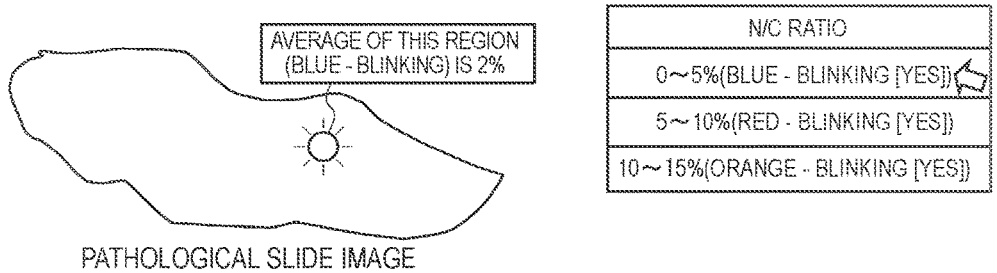
Figure 10C:
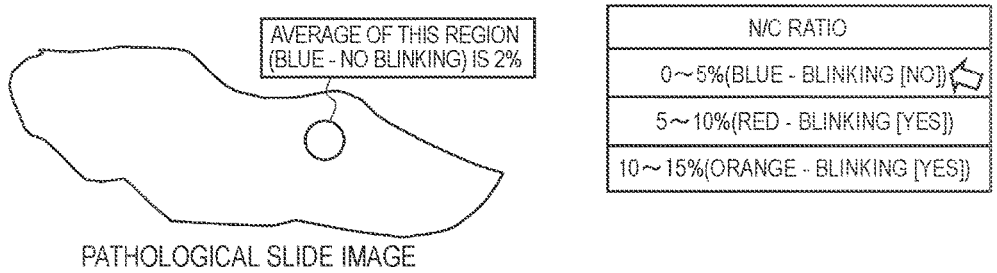

In the case of diagnosing cancer invasion distance, as a selection of a classified disease stage, any one of numbers displayed according to distance in a "cancer index list" of FIGS. 9A and 9B are selected.

Since a pathological index cursor according to an embodiment of the present disclosure enables the user or the like to make a move, rotation, and the like of the displayed pathological index cursor (see a pathological index cursor of FIGS. 9A and 9B), it is possible to easily perform a cancer diagnosis operation.

Also, a pathological index cursor can be provided at a plurality of positions, and the user can use each pathological index cursor by selecting the pathological index cursor through appropriate clicking or the like upon use of the pathological index cursor.

Further, the user or the like can select the whole image (thumbnail image) displayed in the display unit 41 and perform a cancer diagnosis operation in the flow as described above using an identifier attached to the selected whole image.

In an existing system, a user refers to a laboratory information system (LIS) and the like for a sample number shown in an image display device. The user checks what a case of a combined image is based on information of the LIS. Also, the user checks transitional tissue and non-transitional tissue in the combined image. By manipulating a cursor, the user designates two points of transitional tissue, and measures the distance. Based on the value measured by the user, the user searches for diagnostic criterion data and the like and determines which stage of cancer is appropriate, ultimately making a cancer diagnosis. Designation of two points is cumbersome for a user, and also, a large amount of data of a combined image places a load on the processing capability of the device, which poses a risk of lowering the processing speed. In such a situation, efficiency in a cancer diagnosis operation of a user deteriorates.

In addition, when there are a plurality of check-up items, it is necessary to make a diagnosis while checking respective criteria, and the diagnosis is made according to the check-up items one at a time, such that efficiency in the diagnosis operation is not good.

However, using an identifier according to the present disclosure, a workload of the image display device 4 itself can be reduced, and it becomes possible to display one or a plurality of cancer case lists that are necessary criteria and a selected pathological index cursor in a display unit.

Also, during a diagnosis, a cancer index list is displayed, and a user can select a pathological index cursor that is considered appropriate from the cancer index list using an identifier without searching for data of complicated criteria.

The selected pathological index cursor can be used in the form of a ruler, a seal, or the like according to a check-up item.

In this way, it is possible to reduce a load of the user and improve efficiency in a cancer diagnosis operation.

Further, when the server 3 and the like is used, an image processing load of the image display device 4 is reduced, and thus the user can smoothly perform the operation even if the image display device 4 displays a plurality of cancer case lists and a cancer diagnosis is made according to a plurality of check-up items. In this way, efficiency in an operation for the user or the like to diagnose a stage of cancer improves.

Further detailed operation of this embodiment will be described below.

[Operation 1a]

In the information provision device 3, data relating to a pathological slide image (combined image), cancer case data, and cancer index list data is held. Specifically, the data response unit 32 of the information provision device 3 links the data relating to the pathological slide image (combined image) and the cancer case data, and holds the data in the information holding unit 33. Also, a cancer case and one or a plurality of cancer case lists are linked, and the data is held in the information holding unit 33.

A user or the like selects a shown image (pathological slide image (combined image), whole image (thumbnail image), or the like) or the slide ID in the image display device 4. Here, the slide ID has been attached to pathological slide image (combined image) data as an identifier.

The display control unit 42 of the image display device 4 makes an inquiry to the data response unit 32 of the information provision device 3 based on the slide ID that is information relating to the pathological slide image. The data response unit 32 searches the information holding unit 33 for a cancer case corresponding to the slide ID, one or a plurality of case lists corresponding to the cancer case, and also data relating to a combined image corresponding to the slide, and finds the data. When no such data is found, the data response unit 32 displays "Not found" or "Do you want to search another storage device?" and stops temporarily.

The various kinds of found data that are necessary for image display are transmitted from the data response unit 32 to the image display device 4. From the various kinds of transmitted data, the information access processing unit 421 in the display control unit 42 recovers data of the cancer case lists, data of the pathological slide image (combined image), and the like. The display combining unit 422 combines these various kinds of recovered data into a combined image and a cancer case list, and displays the combined image and the cancer case list in the display unit 41. Also, the display combining unit 422 acquires data relating to a size of a sample serving as a target, and decides a size of an appropriate pathological index cursor for the combined image and a cancer index in advance.

In addition, when the user or the like selects a classified disease stage in the cancer case list through clicking, a pathological index cursor corresponding to the clicked portion is selected and displayed (for example, see FIGS. 9A, 9B, 10A, 10B and 10C).

When the user selects a pathological index cursor in the form of a ruler, the user performs a cancer diagnosis operation by making a move, rotation, and the like of the pathological index cursor.

When the user selects a pathological index cursor in the form of a seal, if a diagnosis result corresponds to a predetermined value range shown in the cancer index list, the pathological index cursor in the form of a seal blinks or varies in color. By means of this, the user performs a cancer diagnosis operation. In addition, the user can remove or add something from or to a screen, select blinking/no blinking, or change a color.

When the user changes a magnification of the combined image, the size of the pathological index cursor is also changed according to the changed magnification.

[Operation 1b]

As in operation 1a, various kinds of data are held in the information provision device 3. Description of operations that are the same as in operation 1a will be omitted.

The image display device 4 holds data relating to an identifier serving as a slide ID—cancer case and a cancer case—one or a plurality of cancer case lists in the HDD 45 or the like.

When a user selects a slide ID in the image display device 4, the display control unit 42 requests data relating to a combined image corresponding to the slide ID and data of one or a plurality of cancer case lists from the data response unit 32 of the information provision device 3.

The data response unit 32 searches the information holding unit 33 of the information provision device 3 for the various kinds of requested data, and transmits the various kinds of data to the image display device 4. The various kinds of data are processed for a combined image and the cancer case lists in the display control unit 42, and displayed in the display unit 41. The user selects a pathological index cursor from disease stages of the cancer case lists, thereby performing a cancer diagnosis operation.

[Operation 1c]

The information processing device 2 may perform imaging of a whole image and partial images, and combine combined images. In this case, data relating to these combined images is transmitted from the information processing device 2 to the information provision device 3, and held in the information holding unit 33.

A subsequent operation may be any of operations 1a and 1b.

[Operation 1d]

The information provision device 3 includes an image generator and an image processing unit with the same function as the image generation unit 22 and the image processing unit 23 of the information processing device 2.

Imaging is performed by the information processing device 2, and data relating to these combined images is transmitted to the information provision device 3. Data relating to a combined image combined with a combined image and the like in an image generation unit and an image processing unit of the information provision device 3 is held in the information holding unit 33.

A subsequent operation may be any of operations 1a and 1b.

Further detailed operation will be described below, but the present technology is not limited to the description.

When a sample of cancer is examined, a disease stage line that a cancer invasion distance or a cancer invasion depth exceeds is important. For example, in the case of stomach cancer, it is an important determination point whether cancer invasion exceeds 5 mm or not. However, in an existing system, it is difficult to make a determination as described above.

The server 3 holds data relating to a pathological slide image and a case (identifier) corresponding to the pathological slide image in connection with each other. Also, the case and a list (identifier) of distance corresponding to the case are held in the server 3.

Based on a slide ID of a slide image (thumbnail image, combined image, or the like) shown in the viewer 4 as an identifier, the server 3 receives an inquiry, and transmits an important list of distance corresponding to the slide image to the viewer 4.

In the display unit 41 of the viewer 4, a pathological index cursor selected from a selected distance list is displayed.

Operation of the server 3 will be described.

The viewer 4 designates a slide ID and makes a request. The data response unit 32 inquires of the slide ID/case data holding unit 332 of the information holding unit 33 based on the slide ID. The slide ID/case data holding unit 332 finds a case corresponding to the slide ID, and further, the information holding unit 33 inquires of the cancer index list holding unit 333 holding a cancer index list about a cancer index list corresponding to the case. The cancer index list holding unit 333 finds the cancer index list corresponding to the case, and replies to the viewer 4 with various kinds of data of these results.

As described above, the data response unit 32 may process data in the relation of data relating to a pathological slide image→a case, and the case→a cancer invasion distance list, and hold the processed data in the information holding unit 33. Also, the data response unit 32 may process data in the relation of data relating to a pathological slide image→a cancer invasion distance list, and hold the processed data. In this case, the data response unit 32 inquires of the cancer index list holding unit 333 about a cancer invasion distance list based on a slide ID, and finds the cancer invasion distance list. In addition, the data response unit 32 replies to the viewer 4 with various kinds of data of these results.

Operation of the viewer 4 will be described.

When data relating to a pathological slide image is acquired, the data selection/acquisition unit of the information access processing unit 421 acquires a cancer invasion distance list of the corresponding slide ID and holds the acquired distance information list.

When the data relating to the pathological slide image is acquired, the request/decoding unit of the information access processing unit 421 transmits the corresponding slide ID to the server 3 and acquires various kinds of data relating to the pathological slide image. After that, the request/decoding unit decodes the data of the slide and holds the decoded data relating to the image.

The display combining unit 422 acquires the distance list and a currently selected distance from the data selection/acquisition unit. Also, the display combining unit 422 acquires the decoded image data from the request/decoding unit. The display combining unit 422 combines and displays the decoded image data, the distance list, and the currently selected distance with a size of a pathological index cursor.

A user performs a cancer diagnosis operation using the pathological index cursor.

FIG. 12 illustrates an example of an overall sequence of the present disclosure.

A slide 01 is selected by a user. First, the viewer 4 acquires distance information on the slide 01. The server 3 replies with a distance list of 5 mm, 10 mm, and 15 mm.

Next, the viewer 4 makes a request for data relating to a pathological slide image of the selected slide 01. The server 3 replies with data relating to a combined image corresponding to the request.

The viewer 4 decodes (recovers) the replied data relating to the combined image, and holds the decoded data in a storage unit.

From the cancer invasion distance list, 5 mm is selected by the user. The viewer 4 displays a pathological index cursor with a size of 5 mm.

This sequence is an example, and for example, any of the distance information and the data may be acquired first.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An image display device including:
a display control unit having a display combining unit that displays one or a plurality of pathological index cursors based on information relating to a pathological slide image.

(2) The image display device according to (1), wherein the display combining unit changes a size of a pathological index cursor according to a magnification of a pathological slide image.

(3) The image display device according to (1) or (2), wherein the display combining unit causes a pathological index cursor to blink and/or vary in color according to classification of cancer stages.

(4) The image display device according to any one of (1) to (3), wherein the display combining unit displays a rotatable and/or movable pathological index cursor.

(5) The image display device according to any one of (1) to (4), wherein the display combining unit displays a pathological slide image and a cancer index list for selecting the pathological index cursor.

(6) The image display device according to (5), wherein the cancer index list is one or two or more types of data selected from cancer invasion distance data, cancer invasion area data, cancer invasion depth data, cancer staining data, nucleo-cytoplasmic ratio data, etiological microbe number data, and cancer stage classification data.

(7) The image display device according to any one of (1) to (6), wherein the display control unit further processes data relating to a pathological slide image, cancer case data, and cancer index list data transmitted from an information provision device including a data response unit that acquires cancer case data and cancer index list data based on the information relating to the pathological slide image, and the image display device displays the pathological slide image and the cancer index list.

(8) The image display device according to (7),
wherein the information provision device further includes an information holding unit that holds data relating to a pathological slide image, cancer case data, and cancer index list data corresponding to the pathological slide image data, and the data response unit acquires the data relating to the pathological slide image, the cancer case data, and the cancer index list data corresponding to the pathological slide image from the information holding unit based on information relating to the pathological slide image, and transmits the acquired data to the display control unit.

(9) An image display system including:
an image display control unit having a display combining unit that displays one or a plurality of pathological index cursors based on information relating to a pathological slide image.

(10) The image display system according to (9), further including an information provision device having a data response unit that acquires cancer case data and cancer index list data corresponding to the cancer case data based on the information relating to the pathological slide image.

(11) A microscope system including:
an image display system including an image display device having a display combining unit that displays one or a plurality of pathological index cursors based on information relating to a pathological slide image.

(12) The microscope system according to (11), wherein the image display system further includes an information provision device having a data response unit that acquires cancer case data and cancer index list data corresponding to the cancer case data based on the information relating to the pathological slide image, and transmits the acquired data to the image display device.

(13) An image processing method including:
displaying one or a plurality of pathological index cursors based on information relating to a pathological slide image.

(14) The image processing method according to (13), further including:
acquiring cancer case data and cancer index list data corresponding to the cancer case data based on the information relating to the pathological slide image; and displaying the pathological slide image and a cancer index list for selecting the pathological index cursors based on the cancer case data and the cancer index list data corresponding to the cancer case data.

(15) The image processing method according to (14), wherein one or a plurality of pathological index cursors selected from the cancer index list are displayed.

(16) The image processing method according to (14), wherein cancer case data corresponding to the data relating to the pathological slide image and cancer index list data corresponding to the cancer case data is acquired based on the information relating to the pathological slide image.

(17) A program causing an image display device to execute:

an information provision function of acquiring and transmitting cancer case data corresponding to information relating to a pathological slide image and cancer index list data corresponding to the cancer case data based on the information; and an image display function of displaying a cancer index list for selecting a pathological index cursor based on the cancer index list data.

(18) A program causing an image display device to execute:

an information provision function of holding data relating to a pathological slide image, cancer case data corresponding to the data relating to the pathological slide image and cancer index list data corresponding to the cancer case data, and acquiring and transmitting cancer case data corresponding to information relating to the pathological slide image and cancer index list data corresponding to the cancer case data based on the information; and an image display function of displaying a cancer index list for selecting a pathological index cursor based on the cancer index list data, and also displaying one or a plurality of pathological index cursors selected from the cancer index list.

What is claimed is:

1. A method, comprising:
causing a display device to display a medical image;
determining navigation data based on metadata of the medical image, wherein
the metadata includes a slide number, and
the navigation data corresponds to a type of cancer corresponding to the medical image; and
causing the display device to display the determined navigation data on the medical image in a form of a ruler, wherein
the display of the navigation data in the form of the ruler is based on at least one of a distance information associated with the type of cancer or an area information associated with the type of cancer,
a display size of the navigation data is adjusted based on a resolution of the medical image, and
the navigation data is rotatable and movable.

2. The method according to claim 1, wherein the medical image is a pathological image.

3. The method according to claim 1, wherein the medical image is an image of one of an organ of a living body, a tissue, or cells.

4. The method according to claim 1, further comprising causing the display device to display the navigation data in a form of a seal, wherein
the display of the navigation data in the form of the seal is based on a calculation of a numeric value of at least one of a number or a ratio related to information associated with the type of cancer.

5. The method according to claim 1, wherein the type of cancer includes one of a case of cancer corresponding to the medical image or a status of the cancer corresponding to the medical image.

6. The method according to claim 5, wherein the case of cancer includes at least one of a stomach cancer, a lung cancer, a colon cancer, a brain tumor, a breast cancer, a cervical cancer, an ovarian cancer, an esophageal cancer, an anal cancer, a liver cancer, a pancreatic cancer, a laryngeal cancer, an oral cancer, a tongue cancer, a thyroid cancer, a kidney cancer, an osteosarcoma, a prostate cancer, a testicular tumor, a renal cell carcinoma, a bladder cancer, a rhabdomyosarcoma, a skin cancer, or a leukemia.

7. A method, comprising:
causing a display device to display a microscopic image;
determining navigation data based on metadata of the microscopic image, wherein
the metadata includes a slide number, and
the navigation data corresponds to a type of cancer corresponding to the microscopic image; and
causing the display device to display the determined navigation data on the microscopic image in a form of a ruler, wherein
the display of the navigation data in the form of the ruler is based on at least one of a distance information associated with the type of cancer or an area information associated with the type of cancer,
a display size of the navigation data is adjusted based on a resolution of the microscopic image, and
the navigation data is rotatable and movable.

8. The method according to claim 7, wherein the microscopic image includes an image of one of medicine, pathology, biology, or materials.

9. An image processing system, comprising:
an imaging device configured to capture an image and generate image data that represents the image; and
a memory configured to store executable code which when executed by a processor, cause the processor to:
cause a display device to display the image data;
determine navigation data based on metadata associated with the image data, wherein
the metadata includes a slide number, and
the navigation data corresponds to a type of cancer corresponding to the image data; and
cause the display device to display the determined navigation data on the image data in a form of a ruler, wherein
the display of the navigation data in the form of the ruler is based on at least one of a distance information associated with the type of cancer or an area information associated with the type of cancer,
a display size of the navigation data is adjusted based on a resolution of the image data, and
the navigation data is rotatable and movable.

10. The method according to claim 1, further comprising causing, based on a cancer stage classification corresponding to the medical image, the display device to at least one of blink the navigation data or change a color of the navigation data.

11. The method according to claim 1, wherein a shape of the navigation data is one a triangular shape, a quadrangular shape, a square shape, an oval shape, or a circular shape.

12. The method according to claim 1, wherein the navigation data is in the form of the ruler with gradations.

13. The method according to claim 7, wherein a shape of the navigation data is one a triangular shape, a quadrangular shape, a square shape, an oval shape, or a circular shape.

14. The method according to claim 7, wherein the navigation data is in the form of the ruler with gradations.

15. The image processing system according to claim 9, wherein a shape of the navigation data is one a triangular shape, a quadrangular shape, a square shape, an oval shape, or a circular shape.

16. The image processing system according to claim 9, wherein the navigation data is in the form of the ruler with gradations.

\* \* \* \* \*